United States Patent [19]

Fang

[11] 4,127,551

[45] Nov. 28, 1978

[54] MIXED ESTERS OF DIBASIC UNSATURATED ACIDS, GLYCOLS AND GLYCIDYL ESTERS

[75] Inventor: James C. Fang, Media, Pa.

[73] Assignee: E. I. Du Pont de Nemours and Company, Wilmington, Del.

[21] Appl. No.: 616,836

[22] Filed: Sep. 25, 1975

Related U.S. Application Data

[62] Division of Ser. No. 338,053, Mar. 5, 1973, Pat. No. 3,928,424.

[51] Int. Cl.² ............... C08K 5/11; C08L 61/22; C08L 61/24; C08L 61/28
[52] U.S. Cl. ................... 260/31.6; 260/31.4 R; 428/460
[58] Field of Search .......... 260/31.4 EP, 31.6, 31.4 R, 260/850, 485 G; 560/199

[56] References Cited

U.S. PATENT DOCUMENTS

| | | | |
|---|---|---|---|
| 3,275,583 | 9/1966 | Kloos | 260/22 |
| 3,414,635 | 12/1968 | Edwards et al. | 260/485 G |
| 3,600,459 | 8/1971 | Vasta | 260/834 |
| 3,609,109 | 9/1971 | Plesske et al. | 260/850 |
| 3,657,384 | 4/1972 | Yoshida et al. | 260/31.4 R |
| 3,668,277 | 6/1972 | Riemhofer et al. | 260/31.6 |
| 3,928,424 | 12/1975 | Fang | 260/485 G |

FOREIGN PATENT DOCUMENTS

| | | | |
|---|---|---|---|
| 942,465 | 11/1963 | United Kingdom | 260/485 G |
| 1,049,155 | 11/1966 | United Kingdom. | |
| 1,168,078 | 10/1969 | United Kingdom. | |

Primary Examiner—Allan Lieberman

[57] ABSTRACT

Mixed esters of dibasic unsaturated acids, glycols and glycidyl esters, when formulated with aminoplast resins, form coating compositions which require little or no organic liquid carrier. These compositions are useful for finishing appliances and automobiles and for general industrial use.

8 Claims, No Drawings

MIXED ESTERS OF DIBASIC UNSATURATED ACIDS, GLYCOLS AND GLYCIDYL ESTERS

CROSS-REFERENCE TO RELATED APPLICATIONS

This application is a divisional of application Ser. No. 338,053, filed March 5, 1973, now U.S. Pat. No. 3,928,424, granted Dec. 3, 1975.

BACKGROUND OF THE INVENTION

There has been much emphasis in recent years on developing coating compositions which do not pollute the atmosphere as they dry. This has become increasingly important with the passage of legislation strictly limiting the amounts and kinds of organic liquids that can be emitted during industrial finishing operations.

The esters of my invention, when formulated with aminoplast resins, form coating compositions which require little or no organic liquid carrier to bring them to application viscosity. My compositions therefore emit a minimum of volatiles into the air as they cure.

Their low liquid content also carries with it additional benefits. Since my compositions have an extremely high film-forming solids content, the saving in shipping costs is considerable. Their high solids content also makes it possible, in spray applications, to apply more of the composition per pass of the spray gun, thereby saving much in labor costs.

My compositions also have the advantage of being compatible with most conventional mill bases used in the paint industry to pigment coating compositions.

In addition, when cured by conventional baking techniques, my compositions give hard, durable, glossy, flexible finishes with excellent adhesion to unprimed metal.

All these properties suit my compositions for use in finishing appliances, metal furniture, wood and plastics, for coil coating operations and for topcoating automobiles.

SUMMARY OF THE INVENTION

The esters of my invention are the mixed esters of unsaturated dibasic acids with glycols and with glycidyl esters. More particularly, my esters are those represented by the structural formula $$HO-\underset{H}{\overset{X}{C}}(CH_2OCH_2)_n \left[\underset{Y}{\overset{Y}{\underset{|}{C}}}\right]_m -O-\overset{O}{\overset{\|}{C}}-Z-\overset{O}{\overset{\|}{C}}-O-\underset{H}{\overset{D_1}{\underset{|}{C}}}-\underset{H}{\overset{D_2}{\underset{|}{C}}}(CH_2)_p(Q)_t R \quad (1)$$

where
X is hydrogen, an alkyl radical of 1–4 carbon atoms or phenyl;
Y is hydrogen, —OH, —CH$_2$OH or an alkyl radical of 1–4 carbon atoms (only one Y can be —OH);

Z is $-\underset{H}{\overset{H}{C}}=\underset{}{\overset{}{C}}-$, $-\underset{}{\overset{H}{C}}=\underset{}{\overset{H}{C}}-$, $-CH_2-\overset{CH_2}{\underset{\|}{C}}-$, or $-\overset{CH_2}{\underset{\|}{C}}-CH_2-$;

D$_1$ is hydrogen or —CH$_2$OH;
D$_2$ is hydrogen or —OH;
(but one of D$_1$ or D$_2$ must be —OH or —CH$_2$OH)
Q is $$-O-\overset{O}{\overset{\|}{C}}-$$

or —O—;
R is an alkyl radical of 4–18 carbon atoms, or a singly, doubly or triply unsaturated hydrocarbon radical of 17 carbon atoms;
$n$ is 0 or 1;
$m$ is 1–5;
$p$ is 0 or 1; and
$t$ is 0 or 1.

The mixed esters I prefer are those represented by formula (1) where
I. (a) X is hydrogen, $n$ is 0, $m$ is 1 Y is hydrogen;
(b) X is hydrogen, $n$ is 0, $m$ is 1 and Y is —CH$_3$ and hydrogen; or
(c) X is hydrogen, $n$ is 0, $m$ is 2 and Y is (1) hydrogen and —OH and (2) hydrogen and hydrogen; and
II. D$_1$ is hydrogen, D$_2$ is —OH, $p$ is 1, Q is $$-O-\overset{O}{\overset{\|}{C}}-,$$

$t$ is 1 and R is $$-\underset{R_3}{\overset{R_1}{\underset{|}{C}}}-R_2$$

where R$_1$ is —CH$_3$ and R$_2$ and R$_3$ are lower alkyl, the total number of carbon atoms in R$_1$, R$_2$ and R$_3$ being 7–11.

Preparation of The Esters

I first react about 1 mol of a suitable dibasic unsaturated acid with about 1 mol of a suitable polyol according to the illustrative equation $$HO-\overset{O}{\overset{\|}{C}}-\underset{H}{\overset{H}{C}}=\overset{}{C}-\overset{O}{\overset{\|}{C}}-OH + HOCH_2-\overset{CH_3}{\underset{|}{C}H}-OH \longrightarrow \quad (2)$$

fumaric acid      propylene glycol $$HO-\overset{O}{\overset{\|}{C}}-\underset{H}{\overset{H}{C}}=\overset{}{C}-\overset{O}{\overset{\|}{C}}-O-CH_2CH-OH \atop \underset{}{\overset{}{CH_3}}$$

I catalyze this reaction with about 0.25%, by weight, of toluenesulfonic acid, phosphoric acid, tetrapropyl titanate or dibutyl tin oxide. I also add about 0.05%, by weight of an addition polymerization inhibitor such as p-methoxyphenol or hydroquinone.

I mix the acid and glycol and then hold this mixture at 135°–146° C. under nitrogen until 1 mol of water has been given off. In the usual case this takes about 45 minutes to 1 hour.

I then react about 1 mol of the resulting intermediate with 0.4 to 1.0 mol of a glycidyl ester, a glycidyl ether or an alkylene oxide, according to the illustrative equation (2)

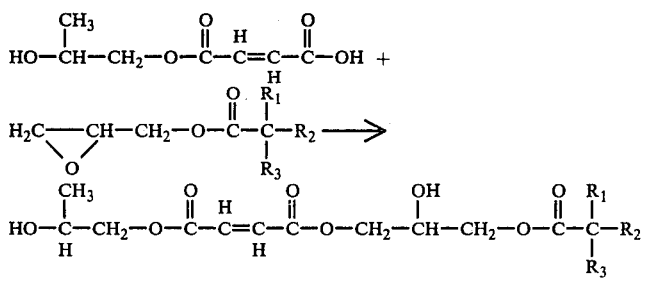

[where $R_1$, $R_2$ and $R_3$ are as in formula (1)].

I mix the reactants and then heat the mixture to 180°–200° C., under nitrogen, and hold it at that temperature for about 1 hour. Preparation of my ester is then complete.

The dibasic unsaturated acids I use in this process are fumaric, maleic and itaconic. Maleic anhydride can also be used.

Illustrative of polyols which can be used are ethylene glycol, 1,2-propanediol, 1,3-propanediol, 1,4-butanediol, 1,5-pentanediol, glycerol, 1,2,3-butanetriol, 1,2,3,4-butanetetrol, 1,6-hexanediol, neopentyl glycol, diethylene glycol, trimethylolpropane and trimethylpentanediol, I prefer to use ethylene glycol, 1,2-propanediol or glycerol.

Illustrative of the glycidyl compounds which can be used are esters of glycidol with monobasic acids of 4–18 carbon atoms, such as glycidyl palmitate, glycidyl laurate and glycidyl stearate; a;kylene oxides of 4–18 carbon atoms such as butylene oxide; and glycidyl ethers such as octyl glycidyl ether.

When R in formula (1) is an unsaturated hydrocarbon radical, I use as the reactant a glycidyl ester represented by the structure

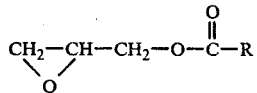

where R is a singly, doubly or triply unsaturated hydrocarbon radical of 17 carbon atoms.

This ester can be prepared by the reaction of a suitable soap with epichlorohydrin. When the soap is derived from a naturally occurring oil such as linseed oil, soya oil, safflower oil, tall oil, or chinawood oil, the glycidyl ester, and the final product it gives, is a mixture of compounds whose R groups vary from each other, the variance of course depending on the nature of the oil.

I especially prefer to use a mixed glycidyl ester known as "Cardura E" ester[1.] which is represented by the structure

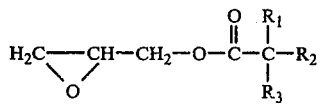

where $R_1$ is —$CH_3$ and $R_2$ and $R_3$ are lower alkyl, the total number of carbon atoms in $R_1$, $R_2$ and $R_3$ being 7–11.

1. Sold by Shell Chemical Company.

It will be apparent from the forgoing equations that small amounts of isomers of the product shown will be formed. For example, when maleic acid is used, the product will partially isomerize to the trans form (fumaric acid).

Also, the hydroxyl group or —$CH_2OH$ [D in formula (1)] which results from rupturing the cyclic ether ring of a glycidyl compound may be attached in either of the positions shown.

In addition, the intermediate, for the most part, opens the cyclic ether ring by reaction with the carboxyl group, as shown in equation (3). However, some rupturing is brought about by reaction with the hydroxyl group on the intermediate. This isomeric form is not represented by formula (1) because such small quantities are produced, but I nevertheless consider it to be a part of my invention.

Similarly, the alkyl groups of X and Y in formula (1) can vary in position according to which hydroxyl group of an unsymmetrical glycol is attacked by the acid when the two are reacted as shown in equation (2).

These isomeric forms can be isolated from the main product by chromatographic techniques, if this is desired. But I have found that isolation is unnecessary because all of the isomers are useful for the purposes I have already described. Indeed, the presence of these isomeric forms in some cases makes the compositions compatible with a wider variety of film-formers and lowers their viscosity. I therefore prefer and recommend that the various isomers not be isolated.

In preparing my esters, one may use mixtures of acids, of glycols and of glycidyl compounds if he wishes to obtain a balance of properties. Suitable mixtures and the amounts in which the components of these mixtures are to be used will be immediately apparent to anyone versed in the polymer or paint art.

How My Mixed Esters Are Used

I mix the product of the foregoing preparation scheme with a conventional aminoplast resin such as a melamine-formaldehyde resin, a benzoguanamine-formaldehyde resin, a urea-formaldehyde resin, a melamine toluenesulfonamide resin, a hexamethoxymethylmelamine resin, or any of the alkylated melamine-formaldehyde, benzoguanamine-formaldehyde or urea-formaldehyde resins. I prefer to use a hexamethoxymethylmelamine resin.

I prepare this mixture so that it contains approximately 50–80%, by weight of the total, of my ester and approximately 20% to about 50%, by weight of the total, of the aminoplast resin.

After the components have been thoroughly mixed, I add a pigment, if this is desired, by way of a conventional mill base. This mill-base can be based, for example, on an alkyd resin or a low molecular weight acrylic resin. The amount of mill base used is conventional and will depend on the depth of color desired. Generally speaking no compatibility problems will be encountered for my coating compositions are compatible with most mill bases conventionally used in the industry. Preparation of the coating composition is then complete.

All that is required to reduce my coating compositions to spray application viscosity is to heat them to approximately 40–55° C. The compositions can also be reduced to spray viscosity by the addition of such conventional thinners as toluene, methylethyl ketone or acetone. In general, this causes no problems for my compositions are also compatible with most such organic liquids. However, I find this dilution to be unnecessary, for it only introduces organic liquids into my compositions which the law now requires to be at low concentration or completely absent, and whose presence confers no advantages.

However my compositions are thinned, they are ordinarily sprayed to whatever substrate is being coated, although other techniques such as brushing, dipping, roller-coating or doctor-blading can be employed. If spray application is the method of choice, those skilled in the art will be pleased to note that no special spraying equipment or techniques are required. My compositions can be conventionally sprayed with no loss of quality or economy.

The thickness to which my compositions are applied is largely a matter of choice, but, as already mentioned, it is possible in most cases to apply somewhat thicker coats than is the rule with conventional coating compositions without the accompanying sagging and running.

My compositions, however they are applied, are then cured by baking the coated articles for approximately ½ hour at 120°–180° C. to give hard, glossy, durable, flexible finishes.

DESCRIPTION OF THE PREFERRED EMBODIMENTS

Those skilled in the polymer and paint art will be able to practice my invention with greater ease after having read the following illustrative examples. I recognize that these artisans will be able to compose numerous variations on the examples' theme, such as the introduction of substituents, not shown here, onto the basic molecule, and the use of conventional adjuncts. I consider all of these variations to be within my inventive concept.

EXAMPLE 1 The following were mixed together in a reaction kettle:

|  | Parts |
| --- | --- |
| Fumaric acid | 116 |
| Propylene glycol | 76 |
| Toluenesulfonic acid | 0.5 |
| p-methoxyphenol | 0.1 |

This mixture was heated to 135°–146° C. and held there for 45 minutes to 1 hour, while approximately 18 parts of water were given off.

"Cardura E" ester, 200 parts, was then added to the reaction mixture over a 2-minute period. The mixture was then held at 180°–200° C. for approximately 1 hour, while 2–3 parts of an impurity in the form of a distillate were collected. The resulting product was an oily straw-colored liquid, having a Gardner-Holdt viscosity of 2–3.

Maleic acid and itaconic acid can be used in place of fumaric acid in this process, in equivalent molar amounts, with substantially the same result. Similarly, ethylene glycol or glycerol can be substituted for propylene glycol.

EXAMPLE 2 The following were thoroughly mixed:

|  | Parts |
| --- | --- |
| Product of Example 1 | 240 |
| Hexamethoxymethylmelamine | 75 |
| Mill base | 540 |
| Composed of |  |
| TiO$_2$ | 63% |
| Non-drying oil alkyd resin (60% solids in toluene xylene 50/50) | 23.5% |
| Toluene | 13.5% |

This mixture was heated to 40°–50° C. and then sprayed to a bonderized, unprimed steel panel to a thickness of 1.5 mils (dry). The panel was baked for ½ hour at 165° C. to give a hard, glossy, durable, flexible, adherent coating.

The products of Example 1 wherein maleic or itaconic acid is substituted for fumaric acid, and where ethylene glycol or glycerol is substituted for propylene glycol, can be used in place of the product of Example 1, in the same amount, with substantially the same result.

I claim:

1. A coating composition comprising, in percent by weight of the total:
   (a) 50–80% of a compound represented by the structure $$X-O-\overset{O}{\underset{\|}{C}}-Z-\overset{O}{\underset{\|}{C}}-O-D-O-\overset{O}{\underset{\|}{C}}-R$$

where
X is the residue of
   ethylene glycol,
   1,2-propanediol,
   1,3-propanediol,
   1,4-butanediol,
   1,5-pentanediol,
   glycerol,
   1,2,3-butanetriol,
   1,2,3,4-butanetetrol,
   1,6-hexanediol,
   neopentyl glycol,
   diethylene glycol,
   trimethylol propane or
   trimethylpentanediol;
Z is

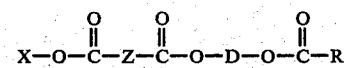

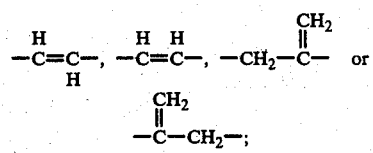

D is

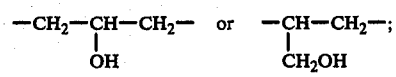

and

R is an alkyl radical of 4–18 carbon atoms, or singly, doubly or triply unsaturated hydrocarbon radical of 17 carbon atoms, and (b) 20–50% of an aminoplast resin.

2. The coating composition of claim 1 wherein X is the residue of ethylene glycol.

3. The coating composition of claim 1 wherein X is the residue of 1,2-propanediol.

4. The coating composition of claim 1 wherein X is the residue of glycerol.

5. The coating composition of claim 1 wherein D is

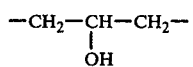

and R is

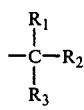

where $R_1$ is $-CH_3$ and $R_2$ and $R_3$ are lower alkyl, the total number of carbon atoms in $R_1$, $R_2$ and $R_3$ being 7–11.

6. The coating composition of claim 2 wherein D is

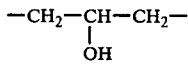

and R is

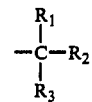

where $R_1$ is $-CH_3$ and $R_2$ and $R_3$ are lower alkyl, the total number of carbon atoms in $R_1$, $R_2$ and $R_3$ being 7–11.

7. The coating composition of claim 3 wherein D is

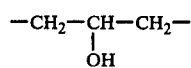

and R is

where $R_1$ is $-CH_3$ and $R_2$ and $R_3$ are lower alkyl, the total number of carbon atoms in $R_1$, $R_2$ and $R_3$ being 7–11.

8. The coating composition of claim 4 wherein D is

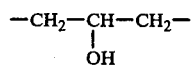

and R is

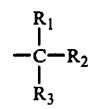

where $R_1$ is $-CH_3$ and $R_2$ and $R_3$ are lower alkyl, the total number of carbon atoms in $R_1$, $R_2$ and $R_3$ being 7–11.

* * * * *